United States Patent
Germain et al.

(10) Patent No.: US 9,254,142 B2
(45) Date of Patent: Feb. 9, 2016

(54) TISSUE EXTRACTION DEVICES AND METHODS

(75) Inventors: Aaron Germain, Campbell, CA (US); Kyle Klein, San Jose, CA (US); Michael D. Walker, Mountain View, CA (US); Benedek Orczy-Timko, Budapest (HU); Balazs Lesko, Budapest (HU)

(73) Assignee: IOGYN, INC., Cupertino, CA (US)

( * ) Notice: Subject to any disclaimer, the term of this patent is extended or adjusted under 35 U.S.C. 154(b) by 676 days.

(21) Appl. No.: 13/442,686

(22) Filed: Apr. 9, 2012

(65) Prior Publication Data

US 2013/0103021 A1 Apr. 25, 2013

Related U.S. Application Data

(60) Provisional application No. 61/474,164, filed on Apr. 11, 2011, provisional application No. 61/501,438, filed on Jun. 27, 2011.

(51) Int. Cl.

| | |
|---|---|
| *A61B 18/18* | (2006.01) |
| *A61B 17/32* | (2006.01) |
| *A61B 17/3205* | (2006.01) |
| *A61B 18/14* | (2006.01) |
| *A61B 18/00* | (2006.01) |
| *A61B 18/12* | (2006.01) |

(52) U.S. Cl.
CPC ... *A61B 17/320016* (2013.01); *A61B 17/32002* (2013.01); *A61B 17/3205* (2013.01); *A61B 18/1482* (2013.01); *A61B 18/1485* (2013.01); *A61B 18/18* (2013.01); *A61B 18/14* (2013.01); *A61B 2017/320028* (2013.01); *A61B 2018/00196* (2013.01); *A61B 2018/00559* (2013.01); *A61B 2018/00595* (2013.01); *A61B 2018/00601* (2013.01); *A61B 2018/122* (2013.01); *A61B 2018/1213* (2013.01); *A61B 2018/1412* (2013.01); *A61B 2217/005* (2013.01)

(58) Field of Classification Search
CPC ........ A61B 18/00; A61B 18/04; A61B 18/08; A61B 18/12; A61B 18/14; A61B 18/18
See application file for complete search history.

(56) References Cited

U.S. PATENT DOCUMENTS

| | | | |
|---|---|---|---|
| 3,850,162 | A | 11/1974 | Iglesias |
| 3,945,375 | A | 3/1976 | Banko |
| 4,203,444 | A | 5/1980 | Bonnell et al. |
| 4,369,768 | A | 1/1983 | Vukovic |
| 4,606,330 | A | 8/1986 | Bonnet |
| 4,955,882 | A | 9/1990 | Hakky |
| 4,998,527 | A | 3/1991 | Meyer |
| 5,009,656 | A | 4/1991 | Reimels |
| 5,080,660 | A * | 1/1992 | Buelna ............................ 606/45 |
| 5,106,364 | A | 4/1992 | Hayafuji et al. |

(Continued)

FOREIGN PATENT DOCUMENTS

WO 2010127174 A1 11/2010

*Primary Examiner* — Christopher D Koharski
*Assistant Examiner* — Elizabeth K So
(74) *Attorney, Agent, or Firm* — Seager, Tufte & Wickhem, LLP

(57) ABSTRACT

A tissue cutting device has an outer sleeve with a distal window and an inner cutting sleeve which moves past the window to cut tissue. The inner cutting sleeve has a lumen which may have a larger proximal diameter than distal diameter. A perimeter of the window may comprise a dielectric material. A distal edge of the inner sleeve may be displaced inwardly.

25 Claims, 15 Drawing Sheets

(56) References Cited

U.S. PATENT DOCUMENTS

| | | | |
|---|---|---|---|
| 5,169,397 | A | 12/1992 | Sakashita et al. |
| 5,195,541 | A | 3/1993 | Obenchain |
| 5,217,479 | A | 6/1993 | Shuler |
| 5,312,399 | A | 5/1994 | Hakky et al. |
| 5,320,091 | A | 6/1994 | Grossi et al. |
| 5,456,689 | A | 10/1995 | Kresch et al. |
| 5,527,331 | A | 6/1996 | Kresch et al. |
| 5,697,281 | A | 12/1997 | Eggers et al. |
| 5,730,752 | A | 3/1998 | Alden et al. |
| 5,759,185 | A | 6/1998 | Grinberg |
| 5,873,886 | A | 2/1999 | Larsen et al. |
| 5,885,277 | A | 3/1999 | Korth |
| 5,906,615 | A | 5/1999 | Thompson |
| 5,941,876 | A | 8/1999 | Nardella et al. |
| 5,997,534 | A | 12/1999 | Tu et al. |
| 6,004,319 | A | 12/1999 | Goble et al. |
| 6,024,751 | A | 2/2000 | Lovato et al. |
| 6,032,673 | A | 3/2000 | Savage et al. |
| 6,056,746 | A | 5/2000 | Goble et al. |
| 6,090,106 | A | 7/2000 | Goble et al. |
| 6,113,594 | A | 9/2000 | Savage et al. |
| 6,149,620 | A | 11/2000 | Baker et al. |
| 6,159,160 | A | 12/2000 | Hsei et al. |
| 6,245,084 | B1 | 6/2001 | Mark et al. |
| 6,293,942 | B1 | 9/2001 | Goble et al. |
| 6,358,263 | B2 | 3/2002 | Mark et al. |
| 6,832,996 | B2 | 12/2004 | Woloszko et al. |
| 6,979,332 | B2 | 12/2005 | Adams |
| 7,226,459 | B2 | 6/2007 | Cesarini et al. |
| 7,244,256 | B2 | 7/2007 | DeCesare et al. |
| 7,249,602 | B1 | 7/2007 | Emanuel |
| 7,678,070 | B2 | 3/2010 | Kumar et al. |
| 7,901,403 | B2 | 3/2011 | Woloszko et al. |
| 7,918,822 | B2 | 4/2011 | Kumar et al. |
| 8,061,359 | B2 | 11/2011 | Emanuel |
| 8,226,549 | B2 | 7/2012 | Kumar et al. |
| 8,267,934 | B2 | 9/2012 | Earley et al. |
| 8,308,726 | B2 | 11/2012 | Kumar et al. |
| 8,388,570 | B2 | 3/2013 | Kumar et al. |
| 8,460,178 | B2 | 6/2013 | Kumar et al. |
| 8,512,283 | B2 | 8/2013 | Kumar et al. |
| 8,568,424 | B2 | 10/2013 | Shugrue et al. |
| 8,574,253 | B2 | 11/2013 | Gruber et al. |
| 8,591,464 | B2 | 11/2013 | Kumar et al. |
| 8,652,089 | B2 | 2/2014 | Kumar et al. |
| 8,663,216 | B2 | 3/2014 | Davison et al. |
| 8,840,625 | B2 | 9/2014 | Adams et al. |
| 8,840,626 | B2 | 9/2014 | Adams et al. |
| 8,893,722 | B2 | 11/2014 | Emanuel |
| 8,951,274 | B2 | 2/2015 | Adams et al. |
| 2004/0230190 | A1 | 11/2004 | Dahla et al. |
| 2006/0047240 | A1 | 3/2006 | Kumar et al. |
| 2006/0122556 | A1 | 6/2006 | Kumar |
| 2006/0122557 | A1 | 6/2006 | Kumar |
| 2007/0021713 | A1 | 1/2007 | Kumar et al. |
| 2008/0021447 | A1 | 1/2008 | Davison et al. |
| 2008/0051708 | A1 | 2/2008 | Kumar et al. |
| 2008/0058588 | A1 | 3/2008 | Emanuel |
| 2008/0058842 | A1 | 3/2008 | Emanuel |
| 2008/0091071 | A1 | 4/2008 | Kumar et al. |
| 2008/0091074 | A1 | 4/2008 | Kumar et al. |
| 2008/0097468 | A1 | 4/2008 | Adams et al. |
| 2008/0097471 | A1 | 4/2008 | Adams et al. |
| 2008/0249366 | A1 | 10/2008 | Gruber et al. |
| 2008/0249553 | A1 | 10/2008 | Gruber et al. |
| 2009/0270812 | A1 | 10/2009 | Litscher et al. |
| 2009/0270895 | A1 | 10/2009 | Churchill et al. |
| 2009/0270896 | A1 | 10/2009 | Sullivan et al. |
| 2009/0270897 | A1 | 10/2009 | Adams et al. |
| 2009/0270898 | A1 | 10/2009 | Chin et al. |
| 2012/0010464 | A1 | 1/2012 | Adams et al. |
| 2012/0172888 | A1 | 7/2012 | Shugrue et al. |
| 2012/0172889 | A1 | 7/2012 | Chin et al. |
| 2012/0197280 | A1 | 8/2012 | Emanuel |
| 2012/0271110 | A1 | 10/2012 | Kumar et al. |
| 2013/0046316 | A1 | 2/2013 | Sullivan et al. |
| 2014/0074136 | A1 | 3/2014 | Emanuel |
| 2015/0012023 | A1 | 1/2015 | Emanuel |

\* cited by examiner

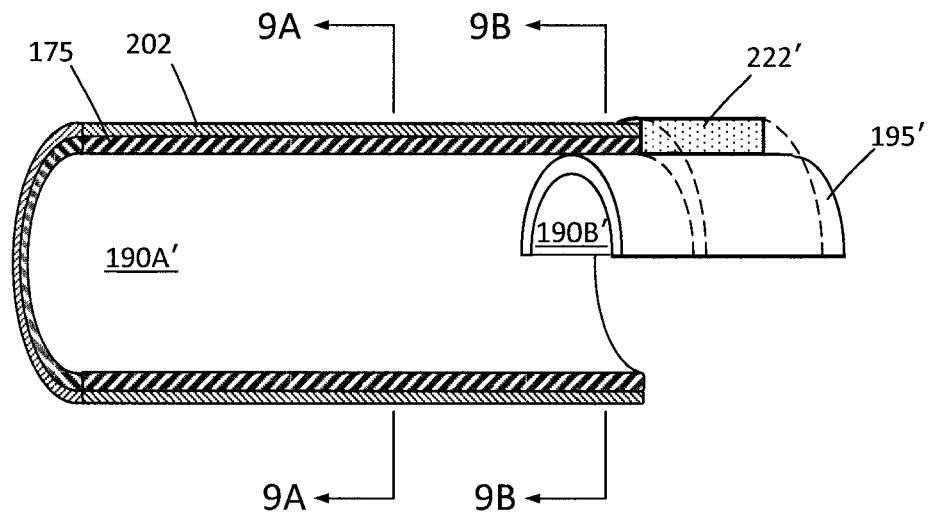
FIG. 8
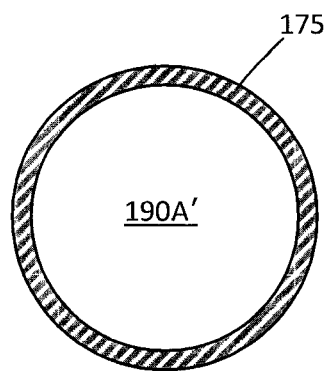 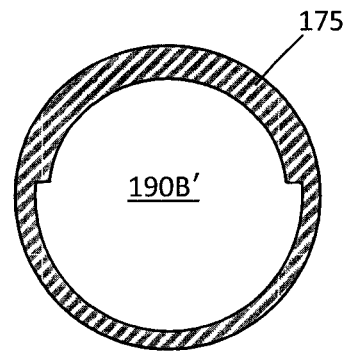
FIG. 9A          FIG. 9B

TISSUE EXTRACTION DEVICES AND METHODS

CROSS-REFERENCE TO RELATED APPLICATIONS

This application claims the benefit of Provisional Application No. 61/474,164, filed Apr. 11, 2011, and Provisional Application No. 61/501,438, filed Jun. 27, 2011. This application is also related to but does not claim priority from patent application Ser. No. 13/277,913, filed Oct. 20, 2011, and patent application Ser. No. 13/287,315, filed Nov. 2, 2011. The entire contents of each of these applications is incorporated herein in its entirety by reference.

FIELD OF THE INVENTION

The present invention relates systems and methods for the cutting and extraction of uterine fibroid tissue, polyps and other abnormal uterine tissue.

BACKGROUND OF THE INVENTION

Uterine fibroids are non-cancerous tumors that develop in the wall of uterus. Such fibroids occur in a large percentage of the female population, with some studies indicating up to 40 percent of all women have fibroids. Uterine fibroids can grow over time to be several centimeters in diameter and symptoms can include menorrhagia, reproductive dysfunction, pelvic pressure and pain.

One current treatment of fibroids is hysteroscopic resection or myomectomy which involves transcervical access to the uterus with a hysteroscope together with insertion of a cutting instrument through a working channel in the hysteroscope. The cutting instrument may be a mechanical tissue cutter or an electrosurgical resection device such as a cutting loop. Mechanical cutting devices are disclosed in U.S. Pat. Nos. 7,226,459; 6,032,673 and 5,730,752 and U.S. Published Patent Appl. 2009/0270898. An electrosurgical cutting device is disclosed in U.S. Pat. No. 5,906,615.

In a myomectomy or hysteroscopic resection, the initial step of the procedure includes distention of the uterine cavity to create a working space for assisting viewing through the hysteroscope. In a relaxed state, the uterine cavity collapses with the uterine walls in contact with one another. A fluid management system is used to distend the uterus to provide a working space wherein a fluid is administered through a passageway in the hysteroscope under sufficient pressure to expand or distend the uterine cavity. The fluids used to distend the uterus are typically liquid aqueous solutions such as a saline solution or a sugar-based aqueous solution.

In some RF electrosurgical resection procedures, the distending fluid is a non-conductive aqueous solution to limit RF current conduction.

One particular concern is the fact that fluid management systems typically administer the fluid under a pressure of up to 100 mm Hg or more which results in a significant risk that the distending fluid may be taken up by a cut blood vessel exposed in the uterine cavity. Such unwanted fluid uptake is known as intravasation, which can lead to serious complications and even death. For this reason, fluid management systems have been developed to monitor the patient's fluid uptake on a continuous basis during a procedure, typically using complicated systems that capture, collect and weigh distending fluids that flow through the uterine cavity.

While hysteroscopic resection can be effective in removing uterine fibroids, many commercially available instrument are too large in diameter and thus require anesthesia in an operating room environment. Conventional resectoscopes require cervical dilation to about 9 mm. What is needed is a system that can effectively cut and remove fibroid tissue through a small diameter hysteroscope.

BRIEF SUMMARY OF THE INVENTION

The present invention comprises a tissue cutting device including an elongated structure where the elongated structure comprises an outer sleeve and an inner cutting sleeve. The elongated structure will typically be attached at a proximal end to a hub, handle, or other component to allow manipulation of the device. The elongated structure will be in the form of a shaft suitable for introduction to a body cavity, for example for transcervical introduction to a uterus. A cutting window will be formed through a wall at a distal end of the sleeve, and the inner sleeve will be configured to move between a proximal position and a distal position relative to the cutting window. In particular, the inner cutting sleeve will typically have a distal cutting edge, such as a sharpened edge, an electrosurgical edge, or the like, which allows the inner sleeve to be advanced past the cutting window in the outer sleeve in order to cut, sever, or otherwise remove tissue which intrudes inwardly through the window. The inner sleeve will have an interior lumen extending at least partly therethrough to allow tissue to be extracted after it has been severed.

In a first aspect of the present invention, the tissue-extracting lumen of the inner cutting sleeve has a distal luminal portion having a first diameter and a proximal luminal portion having a second diameter. The first distal diameter will usually be less than the second proximal diameter so that the cross-sectional area of the distal portion is less than that of the proximal portion of the lumen.

Usually, the distal lumen portion will have a length which is only a small fraction of the length of the total tissue-extracting lumen. The total length of the tissue-extracting lumen for a device configured for transcervical introduction into a uterus, including both the distal and proximal luminal portions, will typically be in the range from 450 mm to 550 mm, with the distal luminal portion with usually extending at least 1 mm from a distal end of the inner cutting sleeve, often extending at least 2 mm from the distal end of the inner cutting sleeve. The distal luminal portion will usually have a maximum length no greater than 15 mm, more usually being no greater than 10 mm. Thus, the distal lumen portion will usually have a length and range from 1 mm to 15 mm, often being in the range from 2 mm to 10 mm.

The inner cutting sleeve and the outer sleeve will typically both be cylindrical at at least their distal ends in order to permit relative rotation and optionally rotational oscillation. In other instances, however, the sleeves or some portion thereof could have non-circular cross-sectional areas where the diameter ranges set forth above will be equivalent to an average width of the lumen in any point. The cross-sectional area of the distal luminal portion will typically be less than 95% of the cross-sectional area of the proximal luminal portion, more usually being less than 90% of the cross-sectional area of the proximal luminal portion. Usually, the cross-sectional area of the distal luminal portion will be less than 95% of the cross-sectional area of the proximal luminal portion, more usually being less than 90% of the cross-sectional area of the proximal luminal portion. The cross-sectional area of the distal luminal portion relative to the proximal luminal portion will typically be in the range from 80% to 95%, more usually in the range from 90% to 95%.

In another aspect of the present invention, a perimeter of the distal or cutting window in the outer sleeve will comprise a dielectric material, such as a ceramic material, a polymeric material, or the like. The dielectric material about the window perimeter functions to provide spacing between the opposing polarity electrode surfaces of the inner cutting sleeve and the outer sleeve.

In a further aspect of the present invention, the inner sleeve of the tissue cutting device has a distal tissue-contacting edge that is displaced radially inwardly from an outer diameter of said inner sleeve, where the displaced edge typically comprises an electrode. In such cases, a dielectric layer will usually be formed on or over an interior of the outer sleeve.

In a still further aspect of the present invention, a ratio of the diameter of at least a proximal portion of the tissue-extraction lumen to the outer diameter of the outer sleeve will be at least 0.65 to 1, usually being at least 0.70 to 1.

In yet another aspect of the present invention, the tissue cutting system will further comprise a hysteroscope, and a ratio of the diameter of the tissue-extraction lumen to an outer diameter of the hysteroscope will be at least 0.35 to 1, preferably being at least 0.4 to 1.

In still another aspect of the present invention, a tissue cutting probe comprises first and second concentric sleeves having a common axis, where the sleeves are configured for relative axial movement between a window-open position for receiving tissue therethrough and a range of window-closing positions in which the second sleeve is adapted to cut tissue which is received through the window in the first sleeve. The probe further comprises a motor to provide relative movement of the sleeves, including rotation, rotational oscillation, and/or axial translation) to effect cutting, and each of the sleeves comprises a tissue-contacting edge, where the contacting edge of one sleeves comprises an electrode and the contacting edge of the other sleeve comprises a dielectric. The dielectric maybe on at least one interfacing surface of the first and second sleeves, and often will be on the surfaces of both the first and second sleeves. Optionally, the first and second sleeves comprise opposing polarity electrodes which maybe coupled to a radiofrequency source.

BRIEF DESCRIPTION OF DRAWINGS

FIG. 8 is a schematic view of a distal end portion of another embodiment of inner RF cutting sleeve.

FIG. 9A is a cross sectional view of the RF cutting sleeve of FIG. 8 taken along line 9A-9A of FIG. 8.

FIG. 9B is a cross sectional view of the RF cutting sleeve of FIG. 8 taken along line 9B-9B of FIG. 8.

DETAILED DESCRIPTION

Figure 1:
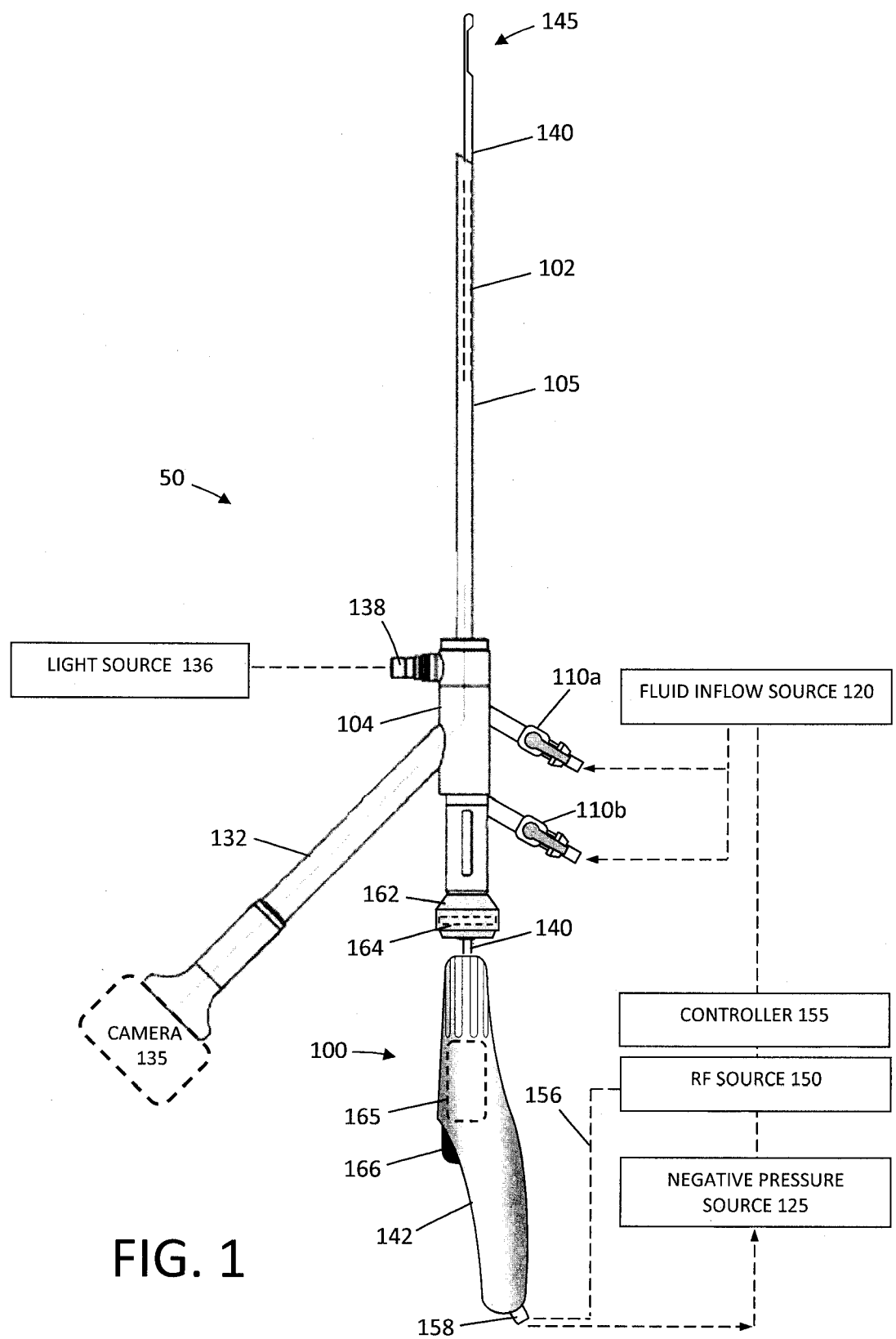
FIG. 1 is a plan view of an assembly including a hysteroscope and a tissue-cutting device corresponding to the invention that is inserted through the working channel of the hysteroscope.
Figure 2:
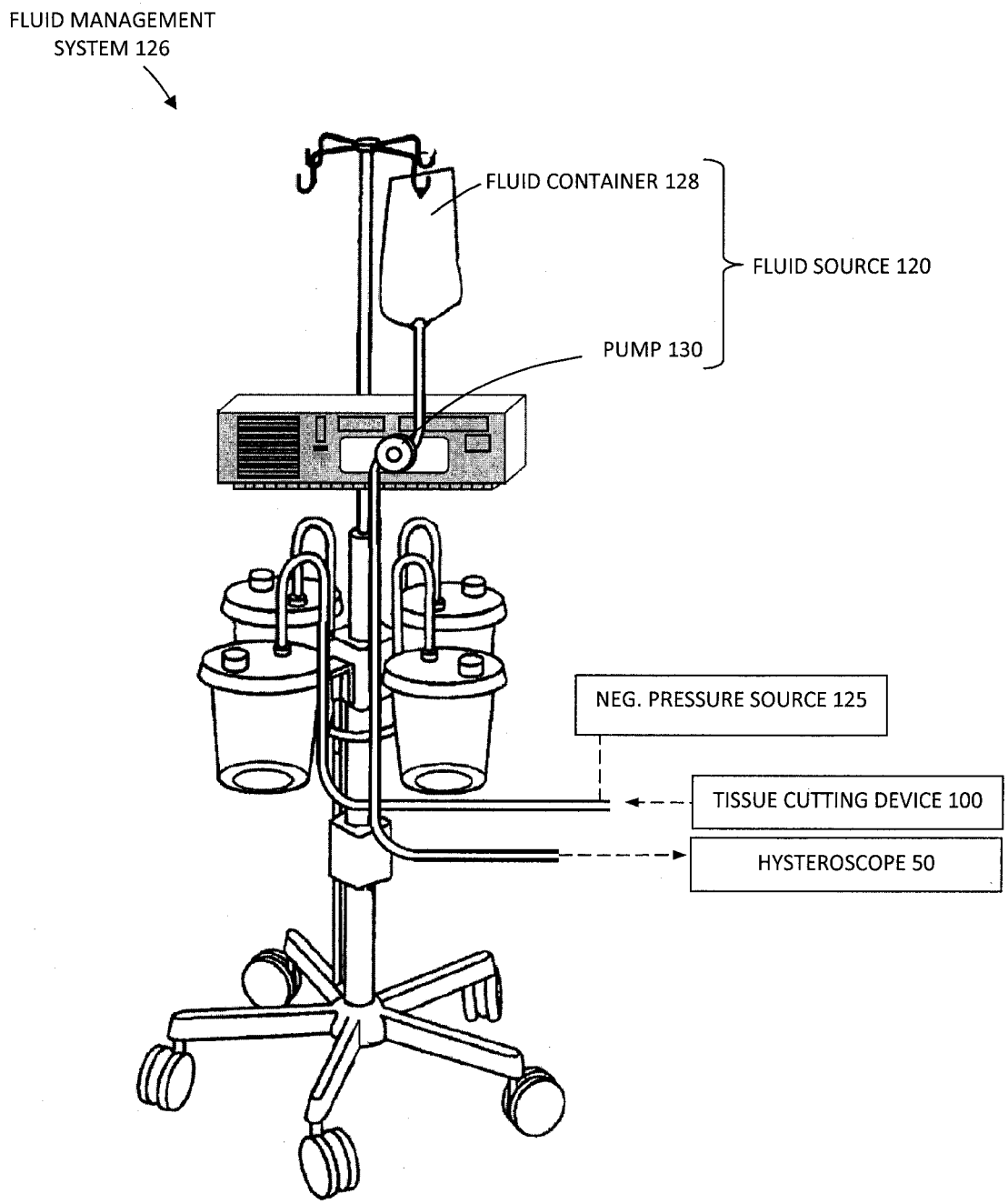
FIG. 2 is a schematic perspective view of a fluid management system used for distending the uterus and for assisting in electrosurgical tissue cutting and extraction.
Figure 3:
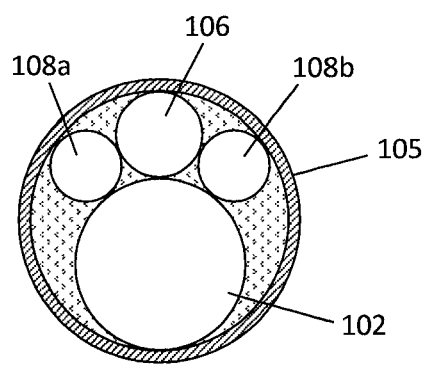
FIG. 3 is a cross-sectional view of the shaft of the hysteroscope of FIG. 1 showing various channels therein.

FIG. 1 illustrates an assembly that comprises an endoscope 50 used for hysteroscopy together with a tissue-extraction device 100 extending through a working channel 102 of the endoscope. The endoscope or hysteroscope 50 has a handle 104 coupled to an elongated shaft 105 having a diameter of 5 mm to 7 mm. The working channel 102 therein may be round, D-shaped or any other suitable shape. The endoscope shaft 105 is further configured with an optics channel 106 and one or more fluid inflow/outflow channels 108a, 108b (FIG. 3) that communicate with valve-connectors 110a, 110b configured for coupling to a fluid inflow source 120 thereto, or optionally a negative pressure source 125 (FIGS. 1-2). The fluid inflow source 120 is a component of a fluid management system 126 as is known in the art (FIG. 2) which comprises a fluid container 128 and pump mechanism 130 which pumps fluid through the hysteroscope 50 into the uterine cavity. As can be seen in FIG. 2, the fluid management system 126 further includes the negative pressure source 125 (which can comprise an operating room wall suction source) coupled to the tissue-cutting device 100. The handle 104 of the endoscope includes the angled extension portion 132 with optics to which a videoscopic camera 135 can be operatively coupled. A light source 136 also is coupled to light coupling 138 on the handle of the hysteroscope 50. The working channel 102 of the hysteroscope is configured for insertion and manipulation of the tissue-cutting and extracting device 100, for example to treat and remove fibroid tissue. In one embodiment, the hysteroscope shaft 105 has an axial length of 21 cm, and can comprise a 0° scope, or 15° to 30° scope.

Still referring to FIG. 1, the tissue-cutting device 100 has a highly elongated shaft assembly 140 configured to extend through the working channel 102 in the hysteroscope. A handle 142 of the tissue-cutting device 100 is adapted for manipulating the electrosurgical working end 145 of the device. In use, the handle 142 can be manipulated both rotationally and axially, for example, to orient the working end 145 to cut targeted fibroid tissue. The tissue-cutting device 100 has subsystems coupled to its handle 142 to enable electrosurgical cutting of targeted tissue. A radio frequency generator or RF source 150 and controller 155 are coupled to at least one RF electrode carried by the working end 145 as will be described in detail below. In one embodiment shown in FIG. 1, an electrical cable 156 and negative pressure source 125 are operatively coupled to a connector 158 in handle 142. The electrical cable couples the RF source 150 to the electrosurgical working end 145. The negative pressure source 125 communicates with a tissue-extraction channel 160 in the shaft assembly 140 of the tissue extraction device 100 (FIG. 4).

FIG. 1 further illustrates a seal housing 162 that carries a flexible seal 164 carried by the hysteroscope handle 104 for sealing the shaft 140 of the tissue-cutting device 100 in the working channel 102 to prevent distending fluid from escaping from a uterine cavity.

In one embodiment as shown in FIG. 1, the handle 142 of tissue-cutting device 100 includes a motor drive 165 for reciprocating or otherwise moving a cutting component of the electrosurgical working end 145 as will be described below. The handle 142 optionally includes one or more actuator buttons 166 for actuating the device. In another embodiment, a footswitch can be used to operate the device. In one embodiment, the system includes a switch or control mechanism to provide a plurality of reciprocation speeds, for example 1 Hz, 2 Hz, 3 Hz, 4 Hz and up to 8 Hz. Further, the system can include a mechanism for moving and locking the reciprocating cutting sleeve in a non-extended position and in an extended position. Further, the system can include a mechanism for actuating a single reciprocating stroke.

Figure 4:
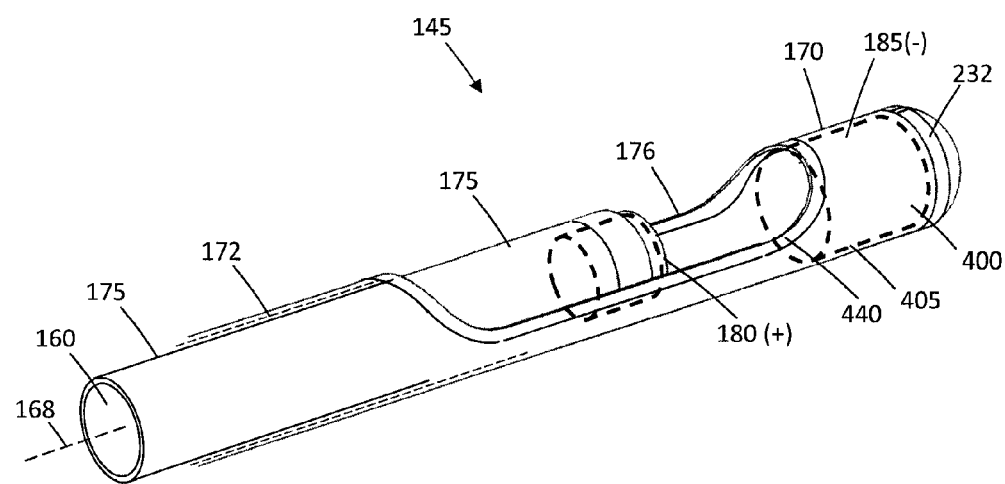
FIG. 4 is a schematic view of the working end of the electrosurgical tissue-cutting device of FIG. 1 showing an outer sleeve with a reciprocating inner cutting sleeve in a partially advanced position.

Referring to FIGS. 1 and 4, an electrosurgical tissue-cutting device has an elongate shaft assembly 140 extending about longitudinal axis 168 comprising an exterior or first outer sleeve 170 with passageway or lumen 172 therein that accommodates a second or inner sleeve 175 that can reciprocate (and optionally rotate or oscillate) in lumen 172 to cut tissue as is known in that art of such tubular cutters. In one embodiment, the tissue-receiving window 176 in the outer sleeve 170 has an axial length ranging between 10 mm and 30 mm and extends in a radial angle about outer sleeve 170 from about 45° to 210° relative to axis 168 of the sleeve. In one embodiment, the window extends in a radial angle of to 180°—that is, the window cut is one-half of the tube. The outer and inner sleeves 170 and 175 can comprise a thin-wall stainless steel material and function as opposing polarity electrodes as will be described in detail below. FIGS. 6A-8 illustrate insulative or dielectric layers carried by the outer and inner sleeves 170 and 175 to limit, control and/or prevent unwanted electrical current flows between certain portions of the sleeve. In one embodiment, a stainless steel outer sleeve 170 has an O.D. of 0.143" with an I.D. of 0.133" and with an inner insulative layer (described below) the sleeve has a nominal I.D. of 0.125". In this embodiment, the stainless steel inner sleeve 175 has an O.D. of 0.112" with an I.D. of 0.106". The inner sleeve 175 with an outer insulative layer 202 has a nominal O.D. of about 0.120 to reciprocate in lumen 172. In other embodiments, outer and or inner sleeves can be fabricated of metal, plastic, ceramic of a combination thereof. The cross-section of the sleeves can be round, oval or any other suitable shape.

In one embodiment, the outer sleeve is 17-7 PH stainless steel has an O.D. of 0.140 to 0.143" with a wall thickness of 0.005" to 0.007" and the inner sleeve also is 17-7. It can be understood that having the largest possible diameter extraction lumen 160 (FIG. 5) is advantageous, but limited by the O.D. of the shaft assembly which in turn is limited by the desired cross section of the hysteroscope 50. To minimize dilation of the patient's cervix, the maximum scope diameter should be about 6.5 mm (0.256") which generally may allow for a maximum working channel of about 0.150". It one aspect of the invention, the thin wall tubing and insulation layers have been developed to provide an optimized tissue extraction lumen diameter (given the above scope dimensions and limitations above) that is greater than 0.090" or greater than 0.100"—all accommodated in hysteroscope having a O.D. of 6.5 mm.

Thus, in general, a tissue cutting device corresponding to the invention comprises an elongated assembly comprising concentric outer and inner sleeves extending along an axis, a tissue-receiving window in the outer sleeve and a reciprocating inner sleeve having a extraction lumen 160 therein (FIG. 5), and wherein the ratio of the diameter of the extraction lumen 160 to the outer diameter of the outer sleeve is at least 0.65:1 or at least 0.70:1.

In another aspect, the tissue cutting device and hysteroscope together corresponding to the invention comprises an assembly or combination wherein the ratio of the diameter of the extraction lumen 160 to the outer diameter of the hysteroscope to at least 0.35:1 or at least 0.40:1.

As can be seen in FIG. 4, the distal end 177 of inner sleeve 175 comprises a first polarity electrode with distal cutting electrode edge 180 about which plasma can be generated. The electrode edge 180 also can be described as an active electrode during tissue cutting since the electrode edge 180 then has a substantially smaller surface area than the opposing polarity or return electrode. In one embodiment in FIG. 4, the exposed surfaces of outer sleeve 170 comprises the second polarity electrode 185, which thus can be described as the return electrode since during use such an electrode surface has a substantially larger surface area compared to the functionally exposed surface area of the active electrode edge 180.

Figure 5:
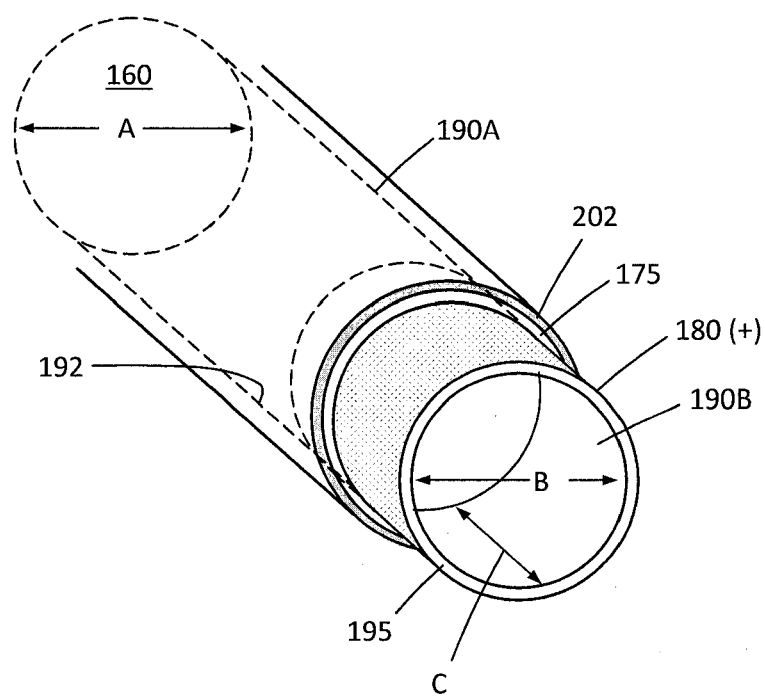
FIG. 5 is a schematic perspective view of the working end of the inner sleeve of FIG. 4 showing its electrode edge.
Figure 6A:
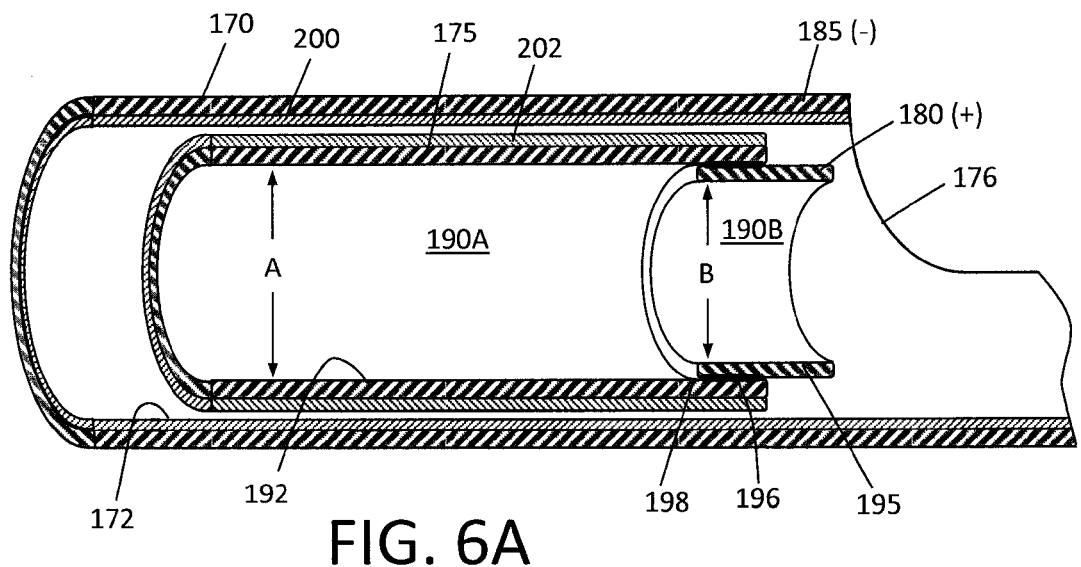
FIG. 6A is a schematic cut-away view of a portion of outer sleeve, inner RF cutting sleeve and a tissue-receiving window of the outer sleeve.

In one aspect of the invention, the inner sleeve or cutting sleeve 175 has an interior tissue extraction lumen 160 with first and second interior diameters that are adapted to electrosurgically cut tissue volumes rapidly—and thereafter consistently extract the cut tissue strips through the highly elongated lumen 160 without clogging. Now referring to FIGS. 5 and 6A, it can be seen that the inner sleeve 175 has a first diameter portion 190A that extends from the handle 142 (FIG. 1) to a distal region 192 of the sleeve 175 wherein the tissue extraction lumen transitions to a smaller second diameter lumen 190B with a reduced diameter indicated at B which is defined by the electrode sleeve element 195 that provides cutting electrode edge 180. The axial length C of the reduced cross-section lumen 190B can range from about 1 mm to 15 mm. In one embodiment, the first diameter A is 0.106" and the second reduced diameter B is 0.095" and has an axial length of 2 mm. In one embodiment, the cross-sectional area of the distal lumen portion is less than 95% of cross-sectional area of the proximal lumen portion, or less than 90% of the cross-sectional area of the proximal lumen portion. As shown in FIG. 5, the inner sleeve 175 can be an electrically conductive stainless steel and the reduced diameter electrode portion also can comprise a stainless steel electrode sleeve element 195 that is welded in place by weld 196 (FIG. 6A). In another alternative embodiment, the electrode and reduced diameter electrode sleeve element 195 comprises a tungsten tube that can be press fit into the distal end 198 of inner sleeve 175. FIGS. 5 and 6A further illustrates the interfacing insulation layers 202 and 204 carried by the first and second sleeves 170, 175, respectively. In FIG. 6A, the outer sleeve 170 is lined with a thin-wall insulative material 200, such as PFA, or another material described below. Similarly, the inner sleeve 175 has an exterior insulative layer 202. These coating materials can be lubricious as well as electrically insulative to reduce friction during reciprocation of the inner sleeve 175.

The insulative layers 200 and 202 described above can comprise a lubricious, hydrophobic or hydrophilic polymeric material. For example, the material can comprise a bio-compatible material such as PFA, TEFLON®, polytetrafluroethylene (PTFE), FEP (Fluorinated ethylenepropylene), polyethylene, polyamide, ECTFE (Ethylenechlorotrifluoroethylene), ETFE, PVDF, polyvinyl chloride or silicone.

Figure 6B:
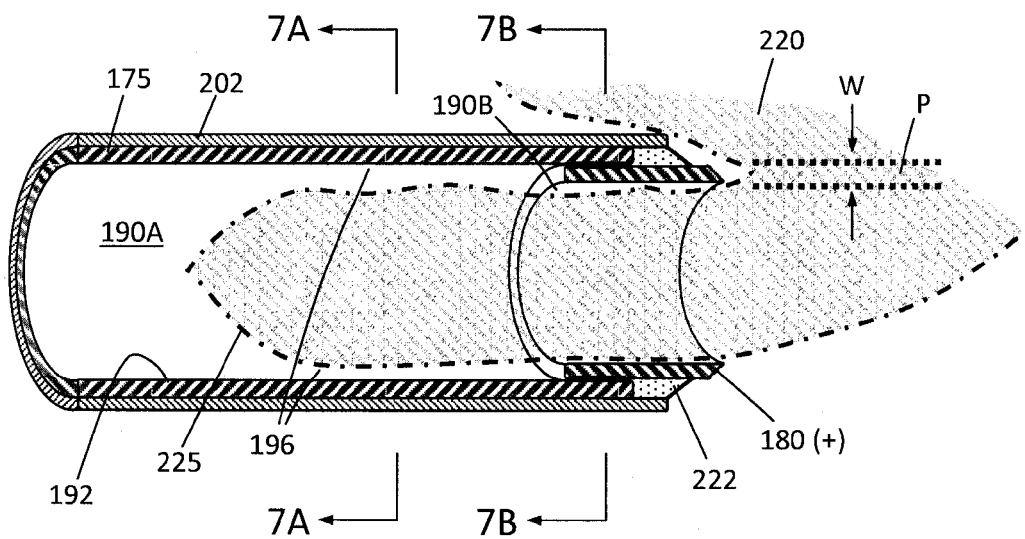
FIG. 6B is a schematic view of a distal end portion another embodiment of inner RF cutting sleeve.

Now turning to FIG. 6B, another variation of inner sleeve 175 is illustrated in a schematic view together with a tissue volume being resected with the plasma electrode edge 180. In this embodiment, as in other embodiments in this disclosure, the RF source operates at selected operational parameters to create a plasma around the electrode edge 180 of electrode sleeve 195 as is known in the art. Thus, the plasma generated at electrode edge 180 can cut and ablate a path P in the tissue 220, and is suited for cutting fibroid tissue and other abnormal uterine tissue. In FIG. 6B, the distal portion of the cutting sleeve 175 includes a ceramic collar 222 which is adjacent the distal edge 180 of the electrode sleeve 195. The ceramic 222 collar functions to confine plasma formation about the distal electrode edge 180 and functions further to prevent plasma from contacting and damaging the polymer insulative layer 202 on the cutting sleeve 175 during operation. In one aspect of the invention, the path P cut in the tissue 220 with the plasma at electrode edge 180 provides a path P having an ablated width indicated at W, wherein such path width W is substantially wide due to tissue vaporization. This removal and vaporization of tissue in path P is substantially different than the effect of cutting similar tissue with a sharp blade edge, as in various prior art devices. A sharp blade edge can divide tissue (without cauterization) but applies mechanical force to the tissue and may prevent a large cross section slug of tissue from being cut. In contrast, the plasma at the electrode edge 180 can vaporize a path P in tissue without applying any substantial force on the tissue to thus cut larger cross-sections of strips of tissue. Further, the plasma cutting effect reduces the cross section of tissue strip 225 received in the tissue-extraction lumen 190B. FIG. 6B depicts a tissue strip to 225 entering lumen 190B which has such a smaller cross-section than the lumen due to the vaporization of tissue. Further, the cross section of tissue 225 as it enters the larger cross-section lumen 190A results in even greater free space 196 around the tissue strip 225. Thus, the resection of tissue with the plasma electrode edge 180, together with the lumen transition from the smaller cross-section (190B) to the larger cross-section (190A) of the tissue-extraction lumen 160 can significantly reduce or eliminate the potential for successive resected tissue strips 225 to clog the lumen. Prior art resection devices with such small diameter tissue-extraction lumen typically have problems with tissue clogging.

In another aspect of the invention, the negative pressure source 225 coupled to the proximal end of tissue-extraction lumen 160 (see FIGS. 1 and 4A) also assists in aspirating and moving tissue strips 225 in the proximal direction to a collection reservoir (not shown) outside the handle 142 of the device.

Figures 7A, 7B:
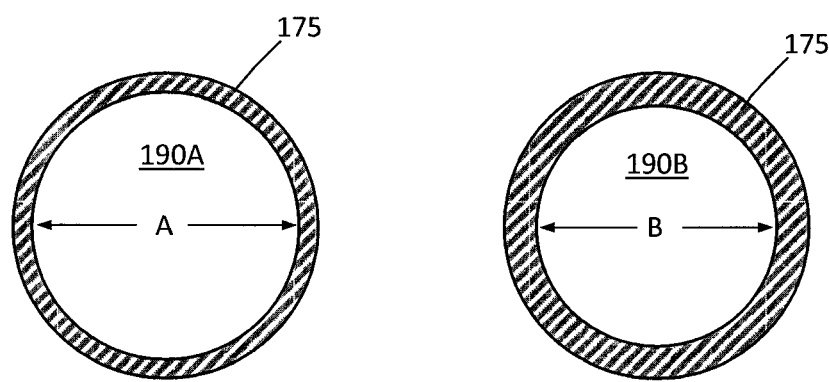
FIG. 7A is a cross sectional view of the inner RF cutting sleeve of FIG. 6B taken along line 7A-7A of FIG. 6B.
FIG. 7B is another cross sectional view of the inner RF cutting sleeve of FIG. 6B taken along line 7B-7B of FIG. 6B.

FIGS. 7A-7B illustrate the change in lumen diameter of cutting sleeve 175 of FIG. 6B. FIG. 8 illustrates the distal end of a variation of cutting sleeve 175' which is configured with an electrode cutting element 195' that is partially tubular in contrast to the previously described tubular electrode element 195 (FIGS. 5 and 6A). FIGS. 9A-9B again illustrate the change in cross-section of the tissue-extraction lumen between reduced cross-section region 190B' and the increased cross-section region 190A' of the cutting sleeve 175' of FIG. 8. Thus, the functionality remains the same whether the cutting electrode element 195' is tubular or partly tubular. In FIG. 8A, the ceramic collar 222' is shown, in one variation, as extending only partially around sleeve 175 to cooperate with the radial angle of cutting electrode element 195'. Further, the variation of FIG. 8 illustrates that the ceramic collar 222' has a larger outside diameter than insulative layer 202. Thus, friction may be reduced since the short axial length of the ceramic collar 222' interfaces and slides against the interfacing insulative layer 200 about the inner surface of lumen 172 of outer sleeve 170.

In general, one aspect of the invention comprises a tissue cutting and extracting device (FIGS. 4A-4B) that includes first and second concentric sleeves having an axis and wherein the second (inner) sleeve 175 has an axially-extending tissue-extraction lumen therein, and wherein the second sleeve 175 is moveable between axially non-extended and extended positions relative to a tissue-receiving window 176 in first sleeve 170 to resect tissue, and wherein the tissue extraction lumen 160 has first and second cross-sections. The second sleeve 175 has a distal end configured as a plasma electrode edge 180 to resect tissue disposed in tissue-receiving window 176 of the first sleeve 170. Further, the distal end of the second sleeve, and more particularly, the electrode edge 180 is configured for plasma ablation of a substantially wide path in the tissue. In general, the tissue-extraction device is configured with a tissue extraction lumen 160 having a distal end portion with a reduced cross-section that is smaller than a cross-section of medial and proximal portions of the lumen 160.

In one aspect of the invention, referring to FIGS. 7A-7B and 9A-9B, the tissue-extraction lumen 160 has a reduced cross-sectional area in lumen region 190A proximate the plasma cutting tip or electrode edge 180 wherein said reduced cross section is less that 95%, 90%, 85% or 80% than the cross sectional area of medial and proximal portions 190B of the tissue-extraction lumen, and wherein the axial length of the tissue-extraction lumen is from 450 mm to 550 mm for access to a uterine cavity. In one embodiment of tissue-cutting device 100 for hysteroscopic fibroid cutting and extraction (FIG. 1), the shaft assembly 140 of the tissue-cutting device is 35 cm in length. Devices used for other procedures can have tissue-extraction lumen that are at least 10 cm, 20 cm, 30 cm or 40 cm in length.

Figure 10A:
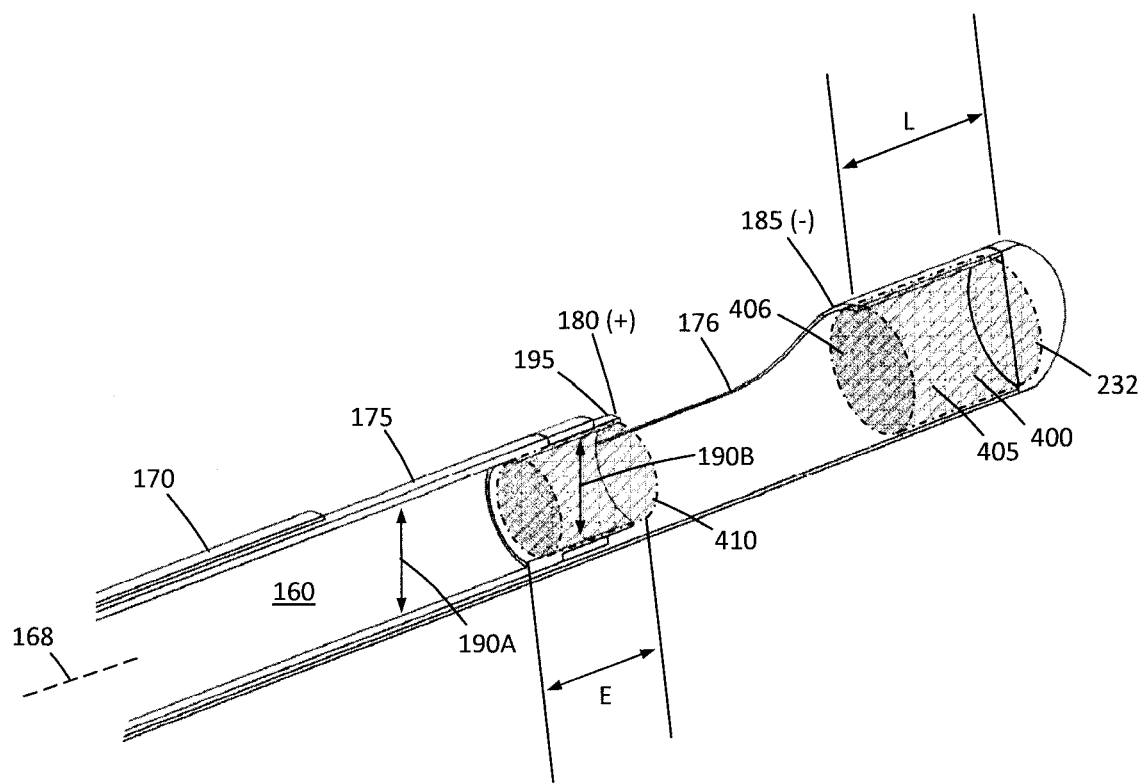
FIG. 10A is an enlarged sectional view of a working end with an RF cutting sleeve in a partially advanced position illustrating fluid volumes that comprise a fluidic pumping mechanism corresponding to the invention for displacement of captured tissue.
Figure 10B:
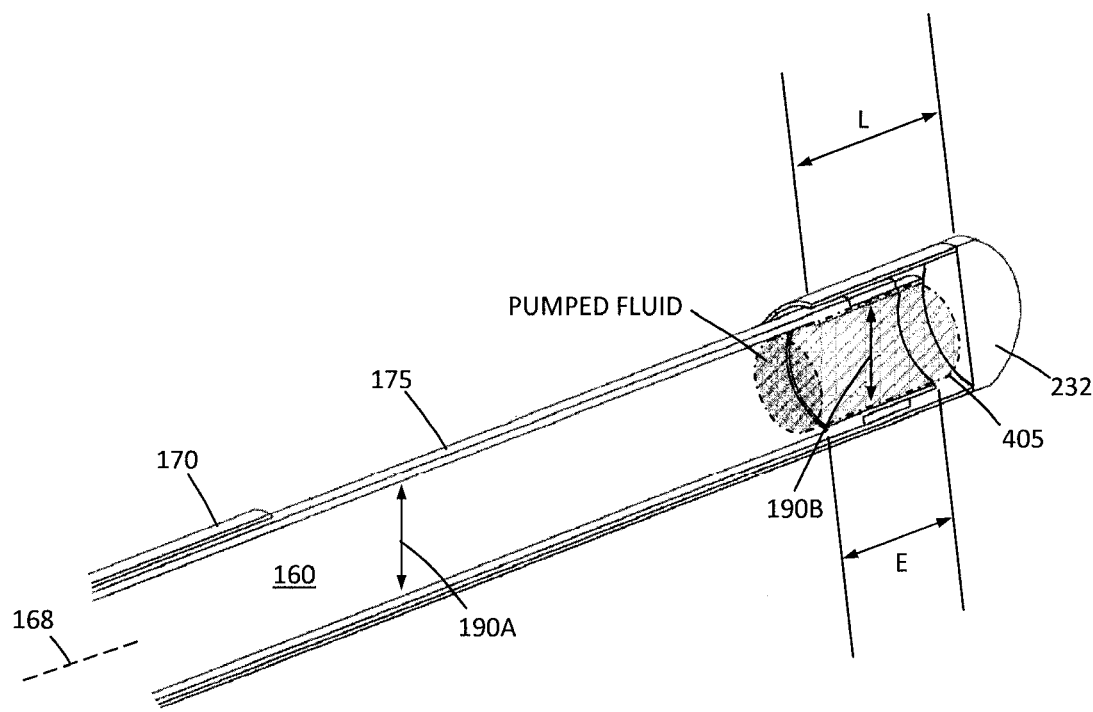
FIG. 10B is another enlarged sectional view similar to FIG. 10A with the RF cutting sleeve in a further advanced position showing how a captured fluid volumes applies fluidic or hydraulic pressure to captured tissue.

Now referring to FIG. 4, FIGS. 10A-10B and FIGS. 11A-11B, one aspect of the invention comprises a "tissue displacement" or pump means that is configured to displace and move tissue strips 225 (see FIGS. 11A-11B) in the proximal direction in lumen 160 of cutting sleeve 175 to thus ensure that tissue does not clog the lumen of the inner sleeve 175. As can be seen in FIGS. 4 and 10A-10B, the pump means as a tissue displacement mechanism comprises a volume of captured fluid indicated at 400 (phantom outline in FIG. 4) that is captured in a terminal chamber 405 of the assembly that is defined by the lumen 172 of outer sleeve and the distal tip or body 232 that is fixedly attached to outer sleeve 170.

As shown in FIG. 10A, the proximal end 406 of the terminal chamber 405 is defined by a plane transverse to axis 168 at the distal edge of the window 176. In one embodiment, the axial length L of the terminal chamber 405 is at least 3 mm, 4 mm of 5 mm. In general, a tissue cutting device comprises an elongated assembly comprising concentric outer and inner sleeves extending along an axis, a tissue-receiving window in the outer sleeve open to an interior lumen that extends to a terminal chamber that is distal to the window, wherein the terminal chamber defines a fluid volume of at least 0.01 mL, at least 0.02 mL or at least 0.04 mL. In one embodiment, the terminal chamber is cylindrical and has a length to diameter ratio of at least 1:1, or at least 1.5:1.

In one embodiment depicted in FIGS. 4 and 10A, the fluid in chamber 405 functions as a fluid piston to pump fluid or tissue in cylindrical chamber 410 defined by the electrode sleeve 195 and the adjoining extraction lumen 160. Of particular interest, the captured fluid 400 can function as a pump and can push a captured tissue strip 225 in the proximal direction from the small cross-section lumen 190B in electrode sleeve 155 as the cutting or inner sleeve 175 moves to its fully advanced or extended position (see. FIG. 10B). For this reason, the above described length L of the terminal chamber 405 is at least as great as the axial length E of the small cross-section lumen 190B in the cutting sleeve 175. Further, as depicted in FIGS. 10A-10B and 11A-11B, the pumping stroke Y of the cutting sleeve 175 extends at least about 3 mm, 4 mm or 5 mm distally beyond the distal edge of the window 290. In another aspect, the stroke Y of the cutting sleeve 175 is at least 5% or 10% of the total stroke of the cutting sleeve (stroke X+stroke Y in FIG. 11A).

In general, a method of cutting tissue corresponding to the invention comprises cutting tissue with a reciprocating cutting sleeve having an extending stroke and a retracting stroke within an outer sleeve, wherein the extending stroke cuts and captures tissue received by a tissue-receiving window in the outer sleeve; and moving the captured tissue proximally in the cutting sleeve with fluidic pressure. The fluidic pressure is provided by the captured fluid volume 400 in chamber 405 in reaction to the relative motion of the fluid volume 400 and the cutting sleeve 175 within which a tissue strip 225 is disposed. As can be understood from FIGS. 10B and 11B, the fluidic pressure is substantially applied when the extending stroke of the sleeve 175 is distal of the window. In one method, the fluidic pressure is applied by a volume of distending fluid from the fluid-immersed working space that is captured in the closed-end terminal chamber 405 of outer sleeve 170. The method includes cutting tissue with an RF plasma at a distal electrode edge 180 of the electrode sleeve 195. In another method, the fluid could be entirely or a partially supplied by a pressurized fluid inflow from a remote source through a flow passageway 415 in outer sleeve 170 as depicted in FIG. 12A, a flow passageway 416 in inner sleeve 175 as depicted in FIG. 12B, or a flow passageway 420 formed intermediate the walls of the outer and inner sleeves 170, 175 as depicted in FIG. 12C.

In one embodiment depicted in FIGS. 4 and 10A, the fluid in chamber 405 functions as a fluid piston to pump fluid or tissue in cylindrical chamber 410 defined by the electrode sleeve 195 and the adjoining extraction lumen 160. Of particular interest, the captured fluid 400 can function as a pump and can push a captured tissue strip 225 in the proximal direction from the small cross-section lumen 190B in electrode sleeve 155 as the cutting or inner sleeve 175 moves to its fully advanced or extended position (see. FIG. 10B). For this reason, the above described length L of the terminal chamber 405 is at least as great as the axial length E of the small cross-section lumen 190B in the cutting sleeve 170. Further, as depicted in FIGS. 10A-10B and 11A-11B, the stroke Y of the cutting sleeve 175 extends at least about 3 mm, 4 mm or 5 mm distally beyond the distal edge of the window 290. In another aspect, the stroke Y of the cutting sleeve 175 is at least 5% or 10% of the total stroke of the cutting sleeve (stroke X+stroke Y in FIG. 11A).

In general, a method of cutting tissue corresponding to the invention comprising cutting tissue with a reciprocating cutting sleeve having an extending stroke and a retracting stroke within an outer sleeve, wherein the extending stroke cuts and captures tissue received by a tissue-receiving window in the outer sleeve, and pushing the captured tissue in the proximal direction in the cutting sleeve with fluidic pressure provided by the captured fluid volume 400 in chamber 405. Further, the fluidic pressure and pump or displacement mechanism is configured to push the captured tissue at least in part from a first smaller cross-section lumen 190B to a second larger cross-section lumen 190A in the cutting sleeve 175. Thereafter, the negative pressure source can more effectively extract and aspirate the tissue from the lumen.

In another aspect and method of the invention, tissue is cut and extracted by (i) interfacing a probe working end with targeted tissue wherein the working end comprises an elongated outer sleeve with a window exposed to a reciprocating inner sleeve, (ii) extending the inner sleeve in a first cutting stroke distally across the window thereby cutting tissue disposed within the window and (iii) extending the inner sleeve in a second pumping stroke distally beyond the window thereby causing fluidic pressure to pump the tissue proximally in a lumen of the inner sleeve. The sequence can be repeated with the first cutting stroke, the second pumping stroke and the retracting stroke having a rate of at least 1 Hz, 2 Hz or 3 Hz. The tissue can be cut with an electrode edge or a blade edge.

In another variation, the terminal chamber 405 is configured to capture a fluid volume sufficient to fill said inner sleeve lumen 160 over a length of at least 3 mm, 4 mm or 5 mm.

In another variation, the cutting step can include applying RF current to generate plasma at an electrode edge 180 on inner sleeve 175 and further comprising the step of terminating RF current at the end of the first cutting stroke. Alternatively, the system and controller 155 can terminate RF current during the second cutting stroke. Alternatively, the controller 155 can terminate RF current during the retracting stroke.

In another variation, the controller can apply RF current to the electrodes during at least a portion of the retracting stroke to thereby cauterize adjacent tissue. The cautery effect can be provided during the retracting stroke at the same operational parameters as used during the first cutting stroke, or at different operational RF parameters than used during the first cutting stroke.

Figure 11A:
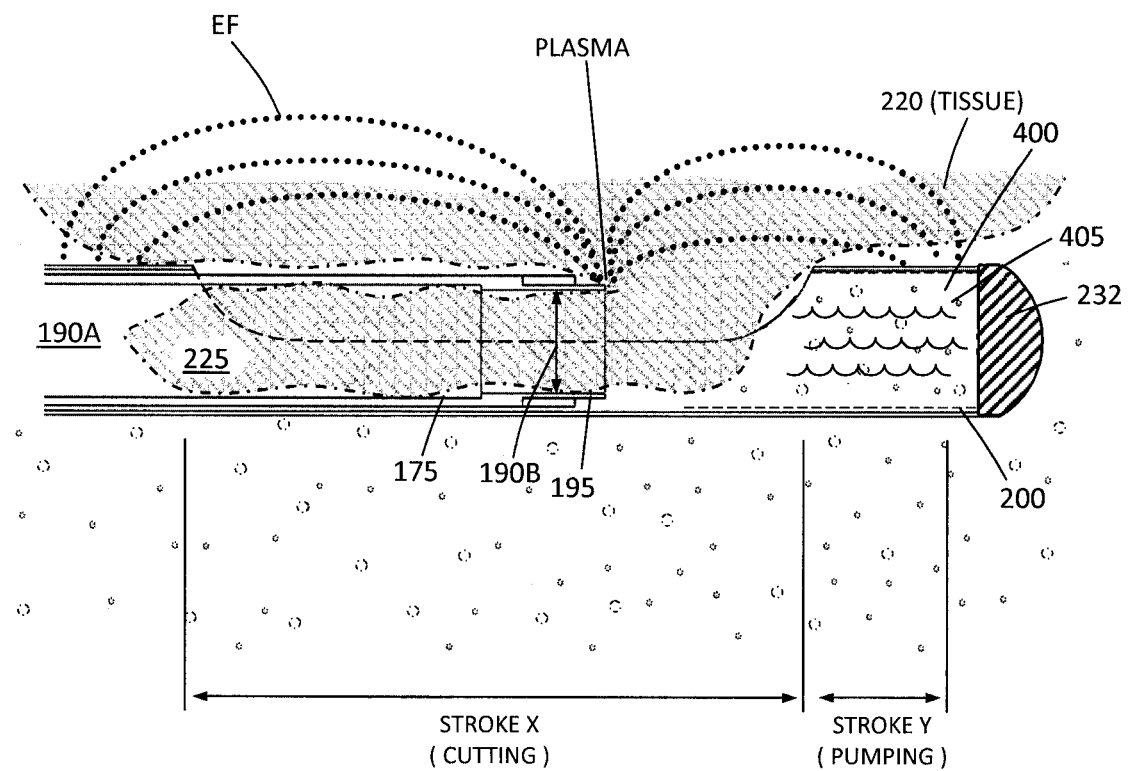
FIG. 11A is a longitudinal sectional view a working end illustrating an electrode edge cutting tissue.
Figure 11B:
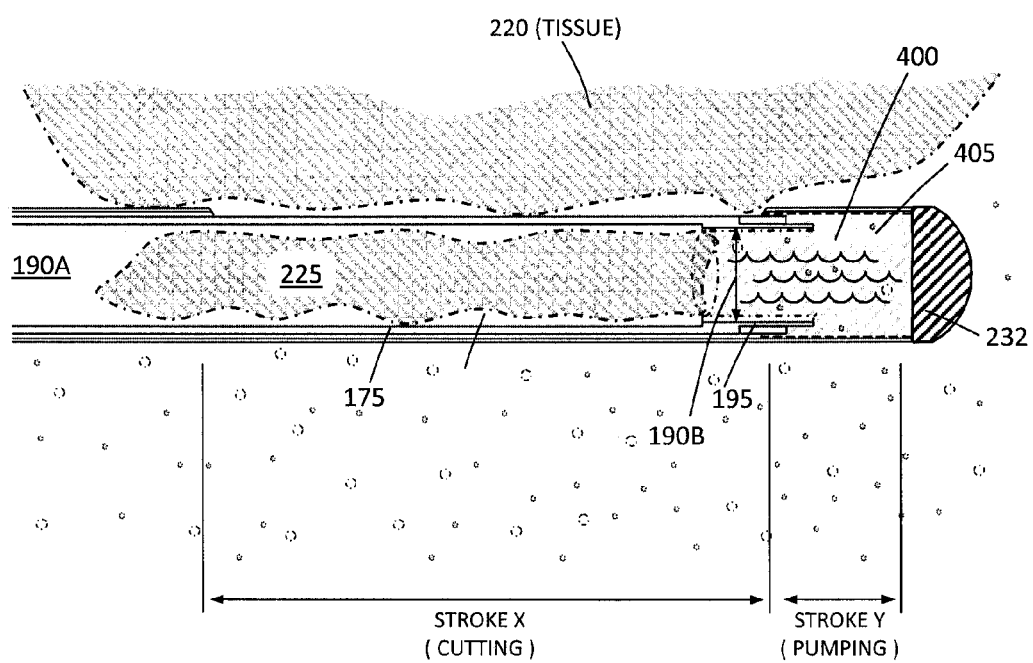
FIG. 11B is a longitudinal sectional view similar to FIG. 11A illustrating the pumping function of the working end.
Figure 12A:
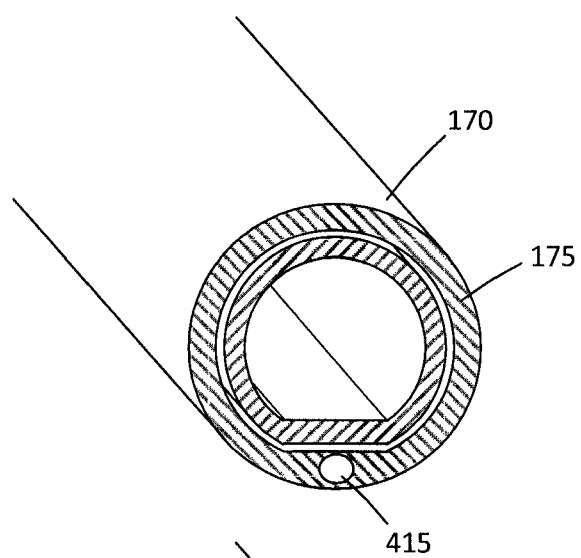
FIG. 12A is a cross-section of a sleeve assembly showing a fluid inflow lumen.
Figure 12B:
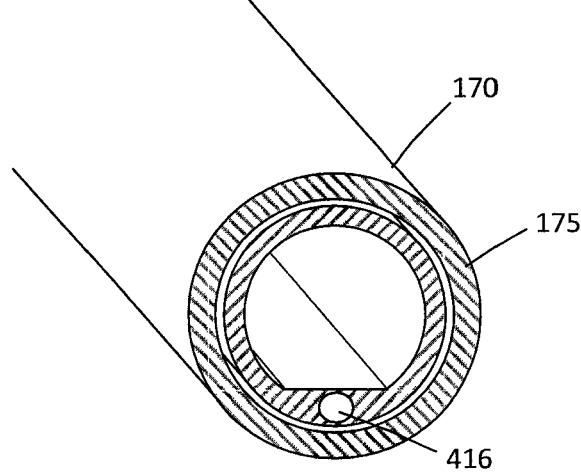
FIG. 12B is a cross-section of a sleeve assembly showing an alternative fluid inflow lumen.
Figure 12C:
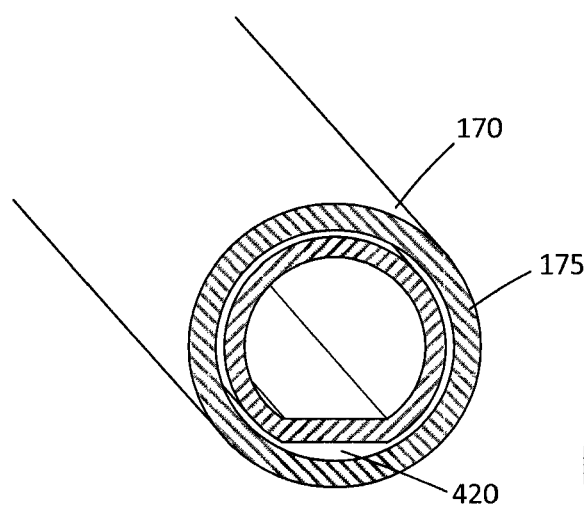
FIG. 12C is a cross-section of a sleeve assembly showing an alternative fluid inflow lumen.

FIGS. 11A-11B illustrate in more detail the functional pump aspects of the invention. In FIG. 11A, the reciprocating cutting sleeve 175 is shown in a medial position advancing distally wherein plasma at the cutting electrode edge 180 is cutting a tissue strip 225 that is disposed within lumen 160 of the cutting sleeve 175. The distending fluid (saline) 244 from the working space migrates through window 176 into terminal chamber 405 to provide the fluid volume that will be captured upon advancement of the cutting sleeve saline.

In FIG. 11A, it can be seen that the system operates in first electrosurgical mode corresponding to the reciprocation and axial range of motion of cutting sleeve 175 relative to the tissue-receiving window 176. The electrical fields EF of the first mode are indicated in FIG. 11A. As described above, the first RF mode can be used over an axial length of travel of inner cutting sleeve 175 as it crosses the tissue-receiving window 176, or the over both the cutting and pumping strokes, and also optionally the retraction stroke.

FIG. 11B illustrates the fluid volume 400 in chamber 405 functioning as a fluid piston and pumping fluid and thus hydraulic or fluidic pressure again tissue strip 225 and moving the tissue proximally relative to the chamber defined by electrode sleeve 195 and the adjoining extraction lumen 160 (cf. FIG. 10B)

In another aspect of the invention, referring back to FIG. 4, the working end comprises first and second converging tissue-contacting edges, 180 and 440, for cutting tissue engaged by or proximate to such edges. In FIG. 4, it can be seen that a first edge comprises the electrode edge 180 described previously. The second first edge 440 comprises an edge of the window 176 that comprises a dielectric or insulative material such as a ceramic of polymeric material. In one embodiment, the tissue cutting probe comprises first and second concentric sleeves having and axis and configured for relative axial movement between a window-open position for receiving tissue therein and a range of window-closing positions in which the second sleeve cuts tissue in a window in the first sleeve, a motor for providing relative movement of the sleeves, wherein each of said sleeves comprising a tissue-contacting edge for contacting tissue, and wherein the contacting edge of one sleeve comprising an electrode and the contacting edge of the other sleeve comprising a dielectric.

In one variation, the tissue cutting probe includes an electrically insulative layer disposed on at least one interfacing surface of the first and second sleeves. In another variation, the tissue cutting probe has an electrically insulative layer disposed the interfacing surfaces of both the first and second sleeves.

In another variation, the interface between the first and second sleeves provides hydraulic resistance to substantially prevent liquid flow therethrough. To provide such hydraulic resistance the electrically insulative layer of one or both sleeves at the interface comprises a hydrophilic surface. In another variation, an electrically insulative layer comprises a hydrophobic surface or an ultrahydrophobic surface.

Figure 13:
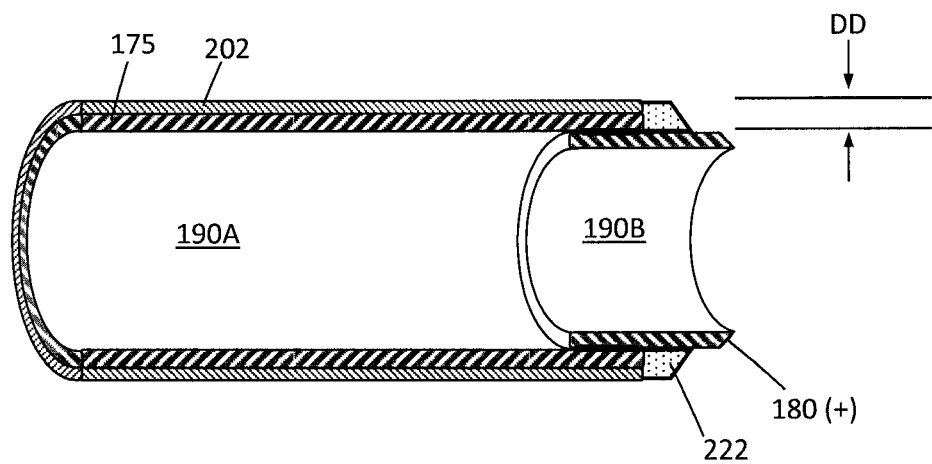
FIG. 13 is a sectional view of a variation of cutting sleeve with an inwardly displaced electrode edge.

Now referring to FIG. 13, in another feature of the invention, it has been found that controlled spacing between the plasma-forming electrode 180 and the return electrode 185 (FIG. 4) is desirable. For this reason, the electrode-sleeve has a displaced tissue-contacting edge 445 that is displaced dimension DD radially inward from an outer diameter of said second or cutting sleeve 175. In general, the tissue cutting probe comprises first and second concentric sleeves having and axis and configured for relative axial movement between a window-open position for receiving tissue therein and a range of window-closing positions in which the second sleeve cuts tissue in a tissue-receiving window in the first sleeve, a mechanism for providing relative movement of the sleeves, and wherein the second sleeve has a displaced tissue-contacting edge that is displaced selected dimension radially inward from a outer diameter of said second sleeve. In one variation, the edge 444 is displaced a dimension DD radially inward of at least 0.003". The inwardly spaced edge further can be configured with a ceramic collar fixed about the exterior of the sleeve proximate to the displaced edge (FIG. 13).

Figure 14:
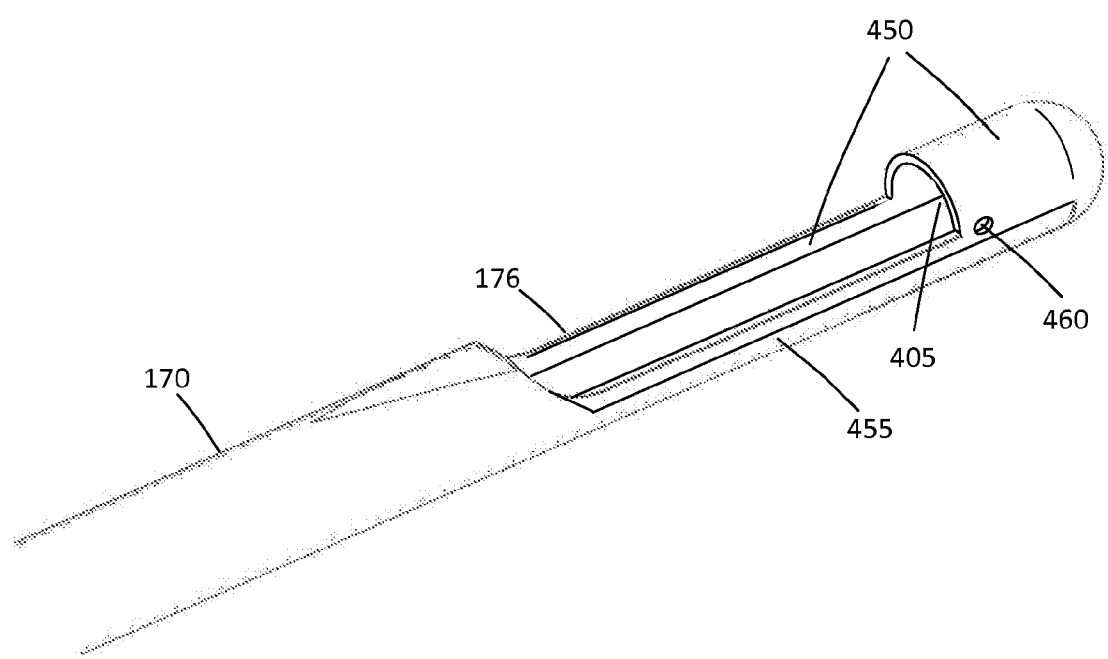
FIG. 14 is a perspective view of another variation with an exterior sleeve with a distal dielectric body portion.

In another aspect of the invention, referring to FIG. 14, the working end 145' can comprise and outer metal sleeve 170 that is coupled to a dielectric body 450 of a ceramic or polymeric material that comprises a thin-wall structure bonded to sleeve 170 and extends substantially around the perimeter of window 176 and provides the interior terminal fluid chamber described above. In another aspect of the invention, the dielectric material provides further spacing between the first polarity electrode surface of the inner cutting sleeve (see. FIG. 4) and the second polarity electrode of the outer sleeve 170 (see FIGS. 4 and 14). A lower portion 455 of the metal sleeve can remain in place to add strength to the structure. In one variation, at least one aperture 460 is provided close to an axially-transverse plane at the distal edge of window 176. Such an aperture can provide for rapid flow of distention fluid into the terminal chamber. Such at least one aperture will be blocked by sleeve 175 during the pumping stroke (see FIG. 11B).

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A tissue resecting device comprising:
   an assembly comprising an outer sleeve with a distal window and an inner sleeve configured to longitudinally reciprocate between a proximal position and a distal position relative to the window during use; and
   wherein the inner sleeve has a distally-facing distal tissue-resecting edge that is displaced radially inwardly from an outer diameter of said inner sleeve, said displaced edge comprising an annular tissue-resecting electrode.

2. The tissue resecting device of claim 1, wherein the displaced edge is displaced radially inward at least 0.003".

3. The tissue resecting device of claim 1, further comprising a dielectric layer on the exterior of the inner sleeve.

4. The tissue resecting device of claim 1, further comprising a dielectric layer on the interior of the outer sleeve.

5. The tissue resecting device of claim 1, further comprising a dielectric material extending around a perimeter of the window.

6. The tissue resecting device of claim 5, wherein the dielectric material comprises a polymeric material.

7. The tissue resecting device of claim 1, wherein the inner sleeve has an interior tissue-extracting lumen with a proximal lumen portion having a first diameter and the electrode includes a lumen having a second diameter less than the first diameter.

8. The tissue resecting device of claim 1, wherein the electrode has a first polarity and a portion of the outer sleeve forms a second electrode having a second polarity opposite the first polarity.

9. A tissue resecting device comprising:
   an outer sleeve including a side window opening into a lumen of the outer sleeve; and
   an inner sleeve positioned in the lumen of the outer sleeve, the inner sleeve comprising:
   a tubular shaft having a tissue extraction lumen extending therethrough, and
   a tubular electrode having an inner diameter and an outer diameter;
   wherein the inner sleeve is configured to longitudinally reciprocate between a proximal position and a distal position relative to the window;
   wherein a proximal portion of the tubular electrode extends into the lumen of the tubular shaft with a distal portion of the tubular electrode extending distally from the tubular shaft;

wherein the outer diameter of the tubular electrode is displaced radially inwardly from an outer diameter of said tubular shaft.

10. The tissue resecting device of claim 9, wherein the tubular electrode includes an annular distal edge.

11. The tissue resecting device of claim 9, further comprising a dielectric material extending around a perimeter of the side window.

12. The tissue resecting device of claim 9, further comprising a dielectric layer on an exterior of the tubular shaft.

13. The tissue resecting device of claim 9, further comprising a dielectric layer on an interior of the outer sleeve.

14. The tissue resecting device of claim 9, wherein the tubular electrode has a first polarity and a portion of the outer sleeve forms a second electrode having a second polarity opposite the first polarity.

15. The tissue resecting device of claim 9, wherein the inner diameter of the tubular electrode is less than a diameter of the tissue extraction lumen of the tubular shaft.

16. A tissue resecting device comprising:
   an outer sleeve including a side window opening into a lumen of the outer sleeve;
   an inner sleeve positioned in the lumen of the outer sleeve, the inner sleeve comprising:
      a tubular shaft having a tissue extraction lumen extending therethrough, and
      a tubular electrode having an inner diameter and an outer diameter;
   wherein a proximal portion of the tubular electrode extends into the lumen of the tubular shaft with a distal portion of the tubular electrode extending distally from a distal end of the tubular shaft;
   wherein the outer diameter of the tubular electrode is displaced radially inwardly from an outer diameter of said tubular shaft;
   wherein the inner sleeve is configured to longitudinally reciprocate relative to the outer sleeve such that the tubular electrode repeatedly moves between a proximal position in which a distal end of the tubular electrode is located proximal of the window and a distal position in which the distal end of the tubular electrode is located distal of the window.

17. The tissue resecting device of claim 16, further comprising a ceramic collar surrounding the tubular electrode distal of the distal end of the inner sleeve.

18. The tissue resecting device of claim 17, wherein the tubular electrode includes an electrode edge located distal of the ceramic collar.

19. The tissue resecting device of claim 18, wherein the electrode edge is a plasma forming edge configured to generate a plasma to resect tissue.

20. The tissue resecting device of claim 16, wherein the tubular electrode is welded to the distal end of the tubular shaft.

21. The tissue resecting device of claim 16, further comprising a dielectric material extending around a perimeter of the side window.

22. The tissue resecting device of claim 16, further comprising a dielectric layer on an exterior of the tubular shaft.

23. The tissue resecting device of claim 16, further comprising a dielectric layer on an interior of the outer sleeve.

24. The tissue resecting device of claim 16, wherein the tubular electrode has a first polarity and a portion of the outer sleeve forms a second electrode having a second polarity opposite the first polarity.

25. The tissue resecting device of claim 16, wherein the inner diameter of the tubular electrode is less than a diameter of the tissue extraction lumen of the tubular shaft.

* * * * *